: US 7,234,586 B1
(45) Date of Patent: Jun. 26, 2007

(54) SELF-CLEANING FOODSTUFF CONVEYORS

(76) Inventor: Paul Bernard Newman, Northcote House, Northlew, Okehampton, Devon EX20 3BT (GB)

( * ) Notice: Subject to any disclaimer, the term of this patent is extended or adjusted under 35 U.S.C. 154(b) by 589 days.

(21) Appl. No.: 10/049,677

(22) PCT Filed: Aug. 17, 2000

(86) PCT No.: PCT/GB00/03175

§ 371 (c)(1),
(2), (4) Date: May 22, 2002

(87) PCT Pub. No.: WO01/11993

PCT Pub. Date: Feb. 22, 2001

(30) Foreign Application Priority Data

Aug. 17, 1999 (GB) ................................. 9919477.1

(51) Int. Cl.
B65G 45/22 (2006.01)

(52) U.S. Cl. ...................... 198/495; 198/496
(58) Field of Classification Search .............. 198/495, 198/496
See application file for complete search history.

(56) References Cited

U.S. PATENT DOCUMENTS

| | | | | |
|---|---|---|---|---|
| 1,543,411 | A | * | 6/1925 | Wittig ......................... 198/495 |
| 3,578,151 | A | * | 5/1971 | Crawford ..................... 198/495 |
| 4,073,376 | A | * | 2/1978 | Krooss ........................ 198/498 |
| 4,363,263 | A | * | 12/1982 | Williams ...................... 99/352 |
| 4,460,427 | A | * | 7/1984 | Haney et al. ................ 156/303 |
| 4,729,468 | A | * | 3/1988 | Pinck ..................... 198/810.02 |
| 5,110,365 | A | * | 5/1992 | Carter .......................... 134/18 |
| 5,303,579 | A | * | 4/1994 | Smith, Jr. ...................... 73/73 |
| 5,355,992 | A | * | 10/1994 | Baig et al. .................. 198/495 |
| 5,449,534 | A | * | 9/1995 | Oishi et al. ................. 427/512 |
| 5,542,525 | A | * | 8/1996 | Kornely ...................... 198/495 |
| 5,597,599 | A | * | 1/1997 | Smith et al. ................. 426/316 |
| 5,613,594 | A | * | 3/1997 | Kootsouradis .............. 198/495 |
| 5,667,926 | A | * | 9/1997 | Maruyama et al. ........... 430/97 |
| 5,783,242 | A | * | 7/1998 | Teague ....................... 426/320 |
| 5,821,546 | A | * | 10/1998 | Xiao et al. ................ 250/458.1 |
| 5,842,504 | A | * | 12/1998 | Schennum et al. ......... 137/540 |
| 5,941,369 | A | * | 8/1999 | Katsura et al. ............. 198/847 |
| 5,960,933 | A | * | 10/1999 | Albrecht .................. 198/689.1 |
| 6,039,922 | A | * | 3/2000 | Swank et al. ................. 422/24 |
| 6,591,970 | B2 | * | 7/2003 | Olson et al. ................ 198/500 |
| 6,592,665 | B2 | * | 7/2003 | Arverus et al. .............. 118/66 |
| 6,710,357 | B1 | * | 3/2004 | Schweitzer .............. 250/492.1 |

(Continued)

FOREIGN PATENT DOCUMENTS

DE           3831419 A1 *    5/1990

(Continued)

Primary Examiner—Joe Dillon, Jr.
(74) Attorney, Agent, or Firm—Stites & Harbison PLLC; Ross F. Hunt, Jr.

(57) ABSTRACT

A conveyor suitable for use, e.g., in food processing apparatus, includes particular procedures and arrangements for decontaminating the surface of the conveyor. The conveyor surface is subject first to a mechanical cleaning, e.g., by spraying of liquid followed by brushing in a rinse/clean unit. This step displaces gross debris from the conveyor surface. In a second step, the surface is subjected to UV irradiation to sterilize the cleaned surface. This UV irradiation may be provided by banks of UV lamps between which the conveyor passes. Detectors for residual organic material may be used to monitor the cleanliness of the surface.

11 Claims, 1 Drawing Sheet

U.S. PATENT DOCUMENTS

| | | | |
|---|---|---|---|
| 6,851,545 B1 * | 2/2005 | Carter | 198/494 |
| 6,964,787 B2 * | 11/2005 | Swart et al. | 426/234 |
| 6,964,788 B2 * | 11/2005 | Phebus et al. | 426/335 |
| 6,971,503 B2 * | 12/2005 | Thompson | 198/494 |
| 7,026,018 B2 * | 4/2006 | Kranovich | 427/521 |

FOREIGN PATENT DOCUMENTS

| | | | |
|---|---|---|---|
| DE | 4442702 A1 | * | 6/1996 |
| FR | 2744920 | * | 8/1997 |
| WO | WO 94/24875 | * | 11/1994 |

* cited by examiner

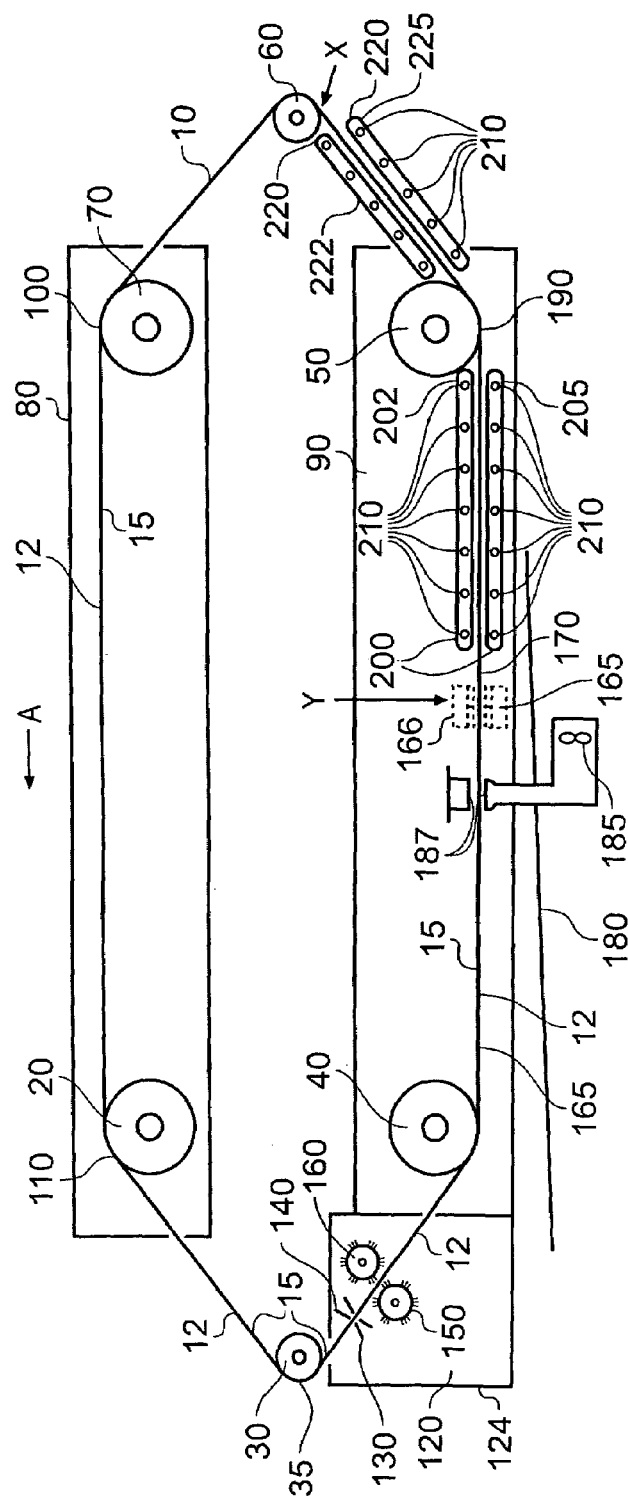
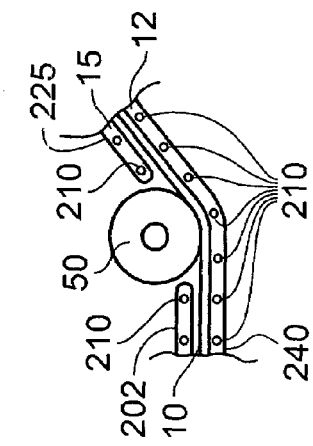
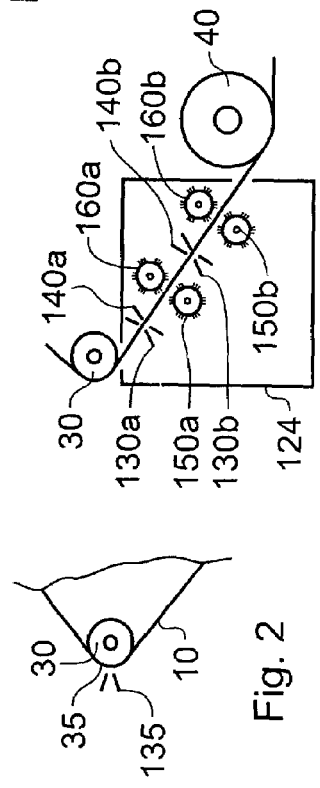
Fig. 1
Fig. 3
Fig. 2
Fig. 4

SELF-CLEANING FOODSTUFF CONVEYORS

FIELD OF THE INVENTION

This invention relates to apparatus and methods for conveying substrates, particularly but not exclusively food. It relates to conveyors that are self-cleaning in that they present a freshly cleaned, decontaminated bed surface to the substrate to be conveyed.

BACKGROUND OF THE INVENTION

The use of conveyors, especially of the continuous belt type, for moving substrates through high throughput manufacturing units is well established. In the food industry, any contact between an item of food and any equipment surface, especially the conveyor, is a potential source of microbial contamination of the food. Furthermore contaminants on the surface of the food can be transferred to equipment leading to cross contamination of subsequent items. The nature of continuous belt conveyors tends to increase the risk of cross contamination, which is of particular concern in the food industry as it can lead to reduced shelf life of the contaminated food item, or even to food poisoning.

Conveyors can be wholly or partly enclosed within a decontaminating unit, for example as described in WO94/24875 (which is incorporated herein by reference) in which a plurality of UV sources are distributed around the walls of a tunnel and directed radially inwardly towards the centre of the cavity through which the substrate is conveyed. The equipment effectively decontaminates the conveyor and the substrate on the conveyor at the same time; although this simultaneous action is often highly desirable from the point of view of food hygiene, it is not universally permitted. Further, in use such equipment can occupy large areas of factory floor, partly because the requirement for ensuring operator safety often entails providing additional features.

Such equipment is effective in minimising the effect of cross contamination between belt and substrate, provided especially that the conveyor belt is apertured or UV transmissive. If the belt is neither apertured nor UV transmissive, decontamination of the underside of the belt can be less effective. Even with belts that are substantially apertured, such as conveyors with belts of interlocking metal or plastic mesh, some contamination can build up in small crevices that are inevitably present in practice, particularly at the flexible nodes of the mesh.

SUMMARY OF THE INVENTION

The present invention provides in one aspect a method of decontaminating a conveying surface of a conveying means comprising a first step of mechanically removing debris, e.g. by one or more of spraying, brushing and scraping; and a second step of subjecting at least substantially all of said surface to UV irradiation. The conveying surface of the conveying means may comprise surface portions of a belt, roller, chain, screw auger or even a food casing such as a sausage skin (which may be used to convey food through a smokehouse or cooker).

There may be a third step of automatically monitoring the cleanliness of the cleaned surface, e.g. by irradiating with suitable radiation and monitoring fluorescence due to contaminants.

Preferably, the radiation used in the second step falls essentially exclusively within the wavelength range 220–300 nm.

Preferably the power is at least 2 W/m$^2$, more preferably at least 5 W/m$^2$. The clearance between said surface and the surface of the nearest source of UV radiation is preferably less than 50 mm, more preferably less than 40 mm, and even more preferably between 25 and 35 mm. If the conveying means is one having a cyclic path including a return run, that is at a stage of the cycle when the direction of movement of the surface is opposite to the direction of conveying, then preferably the method is applied during the return run. If the conveying surface is provided by means having a reverse surface (as is the case with a belt or chain conveyor), then preferably, the method is applied to both the conveying and reverse surfaces, preferably at substantially the same time. If the conveying surface is displaced by means of drive and/or guide rollers, least part of the radiation is preferably directed to either the initial contact point between the surface and a drive or guide roller, or to the final contact point between the surface and a drive or guide roller, or to both said contact points.

At least part of the radiation is preferably applied to a conveying surface while a reverse surface is in contact with a drive roller or a guide roller, especially at a flexure of the conveying surface. This is a particularly preferred way of decontaminating a surface provided by a web of interlocking metal or plastic mesh because the mesh opens slightly as it moves around the roller circumferentially. This opening of the mesh allows radiation to reach into the crevices at the nodes of the mesh that are otherwise occluded.

The UV irradiation can be used to greatest effect if it is applied to a surface free of gross debris, such as particles of food. Therefore, irradiation is preceded by an operation intended to remove such debris, for example by directing jets or sprays of suitable fluid onto the surface. The term "suitable fluid" is to be understood to mean a fluid suitable for the material of the conveying means as well as the substrate conveyed, and as such includes water and water containing cleaning aids such as detergents and other surfactants. With debris from some foodstuffs, for example sugars from fruit or fat from meat, it may be desirable to use heated water, at or above about 65° C., to facilitate removal of the debris. In some circumstances, steam or super-heated steam may be considered suitable fluids or sources thereof.

Debris may alternatively or additionally be removed from the surface by brushing or scraping.

The preliminary cleaning will do a better job the more vigorous the regime, i.e. hot instead of cold, surfactant and water rather than just water, brushing and spraying rather than either spraying or brushing.

The UV will do a better job the higher the energy, i.e. 5 W/m2 as opposed to 2 W/m2 and a longer rather than shorter dwell time.

However the synergism comes in the combined effect. Washing alone will not sterilise the belt although it can make it very clean. UV alone will not sterilise the belt—the reason being that the UV has minimal penetration capability irrespective of energy level—what you will get is a sterile belt where there is no debris and a sterile surface to the debris where there is debris. However the moment the surface of the debris is disturbed, e.g. product falling on or across it, the sterile surface is moved exposing unsterile debris below. It needs effective cleaning and UV treatment to create a sterile, clean belt.

Since any liquid that remains on the surface after spraying is likely to absorb at least some of the UV during irradiation, which will tend to reduce the efficacy of decontamination of the surface, it may be desirable to include in the apparatus a means of removing excess liquid.

The number of jets, sprays, brushing and scraping implements and excess liquid removal means is dependent on the size and travel speed of the conveyor system with larger and faster systems requiring a greater number. In a preferred embodiment, a conveyor according to the present invention comprises a suitably supported belt, means for removing debris from at least one surface of the belt, and one or a plurality of UV sources arranged to irradiate said surface. The means for removing debris and the UV sources are located so as to be able to act on the belt during the return run of the belt. The means for removing debris may comprise one or a plurality of means for directing pressurised liquid onto the surface of the belt. The means for removing debris may comprise, or preferably may further comprise, means for scraping or wiping the surface of the belt. The means for removing debris may comprise a rinse/clean unit, comprising a water spray assembly and a pair of counter rotating brush assemblies.

Alternatively or additionally there may be at least one means for directing pressurised liquid onto the surface of a belt located so as to direct the liquid onto the surface of the belt at a flexure of the belt.

Optionally, means for removing excess liquid from either or both belt surfaces are located between the rinse/clean unit and the UV sources.

In large conveyor systems or systems with fast moving conveying surfaces, there may be provided means for removing debris and/or means for directing pressurised liquid and/or means for removing excess of liquid at a plurality of points around the system. This might include for example two or more rinse/clean units of the kind mentioned above. They may share a common liquid containment chamber. The UV sources are preferably provided as one or a plurality of arrays of UV lamps, each said array being directed to irradiate a conveying surface. Preferably, if the conveyor has conveying and reverse surfaces, the arrays of UV lamps are arranged in pairs (the term "bank" is used hereinafter to refer to a pair of arrays) such that the conveying and reverse surfaces are irradiated at substantially the same time. Preferably, one pair of said arrays is located directly upstream of a drive or guide roller such that at least part of the radiation from the UV lamps of said pair of arrays is directed to the initial contact point between a surface of the belt and said drive or guide roller. Preferably, one pair of said arrays, or more preferably a second pair of said arrays, is located directly downstream of a drive or guide roller such that at least part of the radiation from the UV lamps of said pair of arrays is directed to the final contact point between a surface of the belt and said drive or guide roller.

The number of banks of lamps provided will depend on the size and rotation speed of the conveyor system. Larger and/or faster rotating systems will require more banks of lamps in order to decontaminate the conveyor system thoroughly.

The arrangement of UV lamps in an array is usually linear, although curved or curvilinear arrays are also contemplated within the invention, especially for providing irradiation at a flexure of the conveyor surface.

Alternatively or additionally there may be at least one array arranged so as to irradiate a conveying surface of the conveyor while a reverse surface is in contact with the circumferential surface of a drive roller or a guide roller, especially at a flexure of the conveyor. With a belt of interlocking mesh, this positioning is intended to allow the radiation to pass between the elements of the interlocking material of the belt.

In preferred embodiments, there is further provided a detection unit for detecting the level of cleanliness of the conveying surface of the conveyor system. This detection method preferably uses UV light, preferably in the range 280–395 nm. Organic matter remaining on the surface will fluoresce in the UV light and this fluorescence can be detected by the detection unit. In the preferred detection unit, unacceptably high levels of fluorescence trigger a response which may be an audio or visual warning to warn the user that the cleaning is insufficient. Ideally this event should be automatically logged. Alternatively or additionally, additional or special cleaning steps including extra spraying, increased spray temperature and additional UV energy may be automatically or manually initiated in response to unacceptable levels of organic matter fluorescence.

Another aspect of the invention is conveying apparatus comprising the above-mentioned means.

A further aspect is a method of modifying a conveyor system by the addition of means as specified above.

A further aspect of the invention provides a conveyor belt surface decontaminating unit, comprising an array of UV lamps arranged on a stand. Preferably, the height of the array and the angle of the array are both adjustable so that the unit may be located into an existing conveying means or conveyor so as to irradiate a surface of a belt of said existing conveying means or conveyor. Such a unit may also comprise debris-removing means of any kind specified herein, e.g. a clean/rinse unit, so that the entire assembly can be retrofitted to an existing conveyor.

A further aspect of the invention provides a conveyor belt decontaminating unit, comprising a bank of UV sources arranged on a stand, the bank comprising a first array of UV lamps and a second array of UV lamps, the stand supporting the first and second arrays of UV lamps such that the said first array is held substantially parallel to the said second array, the relative positions of the first and second arrays defining an aperture or slit between the first and second arrays suitable for receiving the conveying element (eg. a belt or an array of chains) of a conveyor. In an embodiment, the vertical height of the slit defined by the arrays is adjustable to accommodate a variety of thicknesses of element, and to allow a suitable clearance between each surface of the element and the surface of the respectively nearest UV lamp when in use. The term "suitable clearance" is to be understood to mean a clearance that allows free passage of the element between the two arrays and also allows adequate UV irradiation to reach the element, and as such will vary according to the circumstances; but is usually less than 50 mm, preferably less than 40 mm, more preferably between 25 and 35 mm.

Some embodiments of the invention will now be described with reference to the drawings.

BRIEF DESCRIPTION OF THE DRAWINGS

In the drawings:

FIG. 1 shows schematically a side elevation of a preferred conveyor according to the present invention;

FIG. 2 shows an alternative location for a liquid dispenser, positioned to direct pressurised liquid onto a belt at a flexure of the belt;

FIG. 3 shows an alternative arrangement of arrays of UV lamps around a flexure of the belt, and FIG. 4 shows an alternative arrangement with double rinse/clean units.

DETAILED DESCRIPTION OF PREFERRED EMBODIMENTS

Referring first to FIG. 1: a conveyor embodying the present invention comprises continuous belt 10 having an upper (or conveying) surface 12 and an under (or non-conveying) surface 15, supported on guide rollers 20, 30, 40, 50, 60 and drive roller 70. It will be appreciated that the number, position, and nature (drive or guide) of the rollers is not crucial for the invention; they are shown as herein for illustration and not restriction.

Belt 10 may be of solid construction, preferably being made from UV receptive or even UV transmissive material to improve cleaning at surface non-uniformities. Additionally or alternatively it may be apertured, for example it may be made of interlocking steel or plastic mesh.

Drive roller 70 drives continuous belt 10 in the conveying direction shown by arrow A, that is in an anti-clockwise direction in FIG. 1 as viewed. Drive roller 70 and guide roller 20, which support belt 10 while conveying, are supported by conveyor frame 80. The corresponding guide rollers 40, 50 support the belt 10 on the return (or non-conveying) run 165 and are supported on conveyor frame 90. Substrate is deposited on belt 10 at point 100 and is conveyed in the direction of arrow A to point 110 where it dismounts. Usually, there will be transfer of micro-organisms from the contact between the substrate and belt 10, some of which will remain on upper surface 12 of belt 10 when the substrate dismounts, accompanied occasionally by other debris. With conventional conveyors, repeated cycles of belt 10 during work shifts can lead to the accumulation of high levels of micro-organisms and accumulation of debris.

Belt 10 continues around guide roller 30 and enters rinse/clean unit 120. Rinse/clean unit 120 comprises liquid dispensing means 130, 140, and counter-rotating brush rollers 150, 160. These are housed in a liquid containment chamber 124 with narrow openings for passage of the belt and a drain (not shown) for collection of run-off liquid and removed debris. The liquid dispensing means are preferably spray bars, i.e. a series of nozzle openings distributed along a conduit for pressurised liquid extending across the conveyor. Belt 10 first encounters a fine spray of suitable liquid from liquid dispensers 130, 140. If the debris is likely to contain "sticky" materials, for example sugars from fruits or fat from meat, it can be desirable to use heated water. A minimum temperature of about 65° C. has been found to be effective. The wetted belt 10 next encounters counter is rotating brushes 150, 160 which remove the gross debris.

The arrangement of rinse/clean unit 120 shown schematically in FIG. 1 is preferred when the material of belt 10 is interlocked, sectional, open grid or mesh, as it is recommended that both surfaces 12, 15 are cleaned. If belt 10 is of solid construction, under-surface spray 140 and its corresponding cleaning brush 160 can be omitted.

As shown in FIG. 2, suitable liquid may be directed from dispensing means 135 onto belt 10 as it moves circumferentially around guide roller 30, for example; that is, the liquid is directed at flexure 35. This arrangement facilitates movement of suitable liquid between the elements of a belt made of interlocking material, which assists removal of debris.

Water (or other suitable liquid, as appropriate) drips from belt 10 as it moves between rinse/clean unit 120 and point 170 of return run 165 into drainage channel 180 and is directed to a suitable drainage point. Drying means, eg using a fan 185 to direct a stream of air (which may be heated) onto the surface of the belts via dryer nozzles 187, may be located after rinse/clean unit 120. The drying means help to ensure the removal of any remaining liquid from the surfaces of the belt, which might otherwise reduce the efficacy of UV decontamination by preventing adequate radiation from reaching the belt's surface.

As belt 10 moves between point 170 and point of contact 190 between roller 50 and belt 10, it receives UV irradiation from a plurality of UV lamps 210 in first irradiation bank 200. First irradiation bank 200 comprises an upper array 202 and a lower array 205 of UV lamps 210 arranged to irradiate both surfaces 12, 15 of belt 10 simultaneously. The clearance between either surface 12, 15 and the surface of the nearest of the UV lamps 210 need be no more than 30 mm, a distance found in trials to be effective in terms of cost and microbial reduction.

If belt 10 is made of interlocking material, or is moving faster than about 10 meters per minute, a second irradiation bank 220 located between rollers 50, 60 is sometimes desirable to ensure that sufficient irradiation passes between the interlocking material of belt 10 as it opens up around the circumference of roller 50 and/or to ensure sufficient exposure to UV to achieve sterility. Belt 10 now passes over roller 60 to roller 70 where the cycle repeats.

Irradiation banks 200, 220 may be supported on conveyor frame 90, or either or both may be supported on free-standing stands.

FIG. 3 shows an alternative arrangement of UV arrays in the region around roller 50 that is especially suitable when the belt is made of interlocking material. Arrays 202 and 225 are arranged, as before, to direct irradiation to the inner surface 15 of belt 10. Array 240 is arranged to irradiate the outer surface 12, especially at the flexure of the belt when the radiation can pass more easily between the elements of the mesh. Array 240 may be supported on or by conveyor frame 90, or it may be mounted on a suitably positioned free-standing stand.

FIG. 4 shows a particularly preferred version with more than one clean/rinse unit. Inside the liquid containment chamber 124 two sets of sprayers/brush rollers are provided, indicated by reference numbers as above supplemented with a, b for the first and second sets respectively.

Referring again to FIG. 1, sensor units 165,166 are shown for detecting residual organic material on the conveyor after the rinse/clean stage. These can be combined UV emitter/sensor units which are known in themselves. They may be positioned at Y to monitor the performance of the rinse/clean arrangement, and/or at X to monitor the performance of the entire cleaning system. Preferably this monitoring is continuous, with its output being logged by a control processor provided as part of the arrangement. It is particularly preferred that this processor is programmed and connected to modify the cleaning regime in dependence on the detected level at residues on the conveyor surface, e.g. to initiate or increase the action of the mechanical cleaner (e.g. by any of more forceful of more rigid brushing, increased liquid spray force or temperature) in response to an increase in detected contaminants, either progressively or in response to a present contamination limit being reached.

The invention claimed is:

1. A self-cleaning conveying arrangement for conveying foodstuffs, said arrangement comprising a conveying device including a conveying surface having a cyclic path, said cyclic path having a conveying run for conveying a foodstuff, and a return run; said conveying device further including a decontamination arrangement arranged to act on said conveying surface in said return run, said decontamination arrangement comprising a first cleaner which comprises a sprayer and is adapted to mechanically remove food debris from the conveying surface, and a second cleaner, downstream of the first cleaner, which subjects said surface to ultraviolet irradiation, so that a freshly cleaned decontaminated conveying surface is returned to the conveying run.

2. A self-cleaning conveying arrangement according to claim 1 in which the conveying device is a belt conveyor.

3. A self-cleaning conveying arrangement according to claim 1 in which the first cleaner includes one or more of brushes and scrapers.

4. A self-cleaning conveying arrangement according to claim 3 in which the sprayer of the first cleaner comprises a rinse/clean unit having liquid directing means for directing liquid onto the conveying surface and in which the first cleaner further comprises a brush or scraper for acting on the conveying surface wetted by the liquid directed thereon by said liquid directing means.

5. A self-cleaning conveying arrangement according to claim 1 in which the second cleaner applies UV radiation right across the conveying surface at a power of at least 2 $W/m^2$.

6. A self-cleaning conveying arrangement according to claim 1 in which said first cleaner and/or said second cleaner acts on the conveying surface at a flexure thereof.

7. A self-cleaning conveying arrangement according to claim 1 comprising a detection unit positioned adjacent the conveying surface downstream of at least the first cleaner, to detect the presence of any residual matter on the conveying surface after the action of said cleaner.

8. A self-cleaning conveying arrangement according to claim 1 wherein said decontamination arrangement includes a liquid containment chamber with entry and exit openings for the conveying device.

9. A self-cleaning conveying arrangement according to claim 1 wherein said second cleaner comprises an array of UV lamps directed to irradiate said conveying surface.

10. A self-cleaning conveying arrangement according to claim 1 including a drying device for drying the conveying surface intermediate the first cleaner and the second cleaner.

11. A self-cleaning conveying arrangement according to claim 1 wherein said second cleaner comprises sources of UV radiation disposed so that the clearance between said conveying surface and the nearest of said sources is less than 50 mm.

* * * * *